US012629242B2

(12) United States Patent
Kauper et al.

(10) Patent No.: US 12,629,242 B2
(45) Date of Patent: May 19, 2026

(54) SYSTEM, APPARATUSES, DEVICES, AND METHODS FOR PACKAGING AN ANALYTE DIFFUSIVE IMPLANTABLE DEVICE

(71) Applicant: Neurotech USA, Inc., Cumberland, RI (US)

(72) Inventors: Konrad A. Kauper, Sutton, MA (US); John F. Mills, Wakefield, RI (US); Sandy Sherman, Fairhaven, MA (US); Arne M. Nystuen, Brookline, MA (US)

(73) Assignee: Neurotech USA, Inc., Cumberland, RI (US)

( * ) Notice: Subject to any disclaimer, the term of this patent is extended or adjusted under 35 U.S.C. 154(b) by 516 days.

(21) Appl. No.: 17/773,159

(22) PCT Filed: Nov. 2, 2020

(86) PCT No.: PCT/US2020/058581
§ 371 (c)(1),
(2) Date: Apr. 29, 2022

(87) PCT Pub. No.: WO2021/087476
PCT Pub. Date: May 6, 2021

(65) Prior Publication Data
US 2024/0180682 A1 Jun. 6, 2024

Related U.S. Application Data

(60) Provisional application No. 62/930,504, filed on Nov. 4, 2019, provisional application No. 62/929,619, filed on Nov. 1, 2019.

(51) Int. Cl.
*A61F 2/02* (2006.01)
*A61F 2/00* (2006.01)
(Continued)

(52) U.S. Cl.
CPC ............ *A61F 2/022* (2013.01); *A61F 2/0095* (2013.01); *A61F 9/0017* (2013.01); *B65D 81/22* (2013.01);
(Continued)

(58) Field of Classification Search
CPC .............................. A61F 2/0095; B65D 81/22
(Continued)

(56) References Cited

U.S. PATENT DOCUMENTS 4,697,703 A * 10/1987 Will ....................... B65D 25/10
206/525
4,892,538 A 1/1990 Aebischer et al.
(Continued)

FOREIGN PATENT DOCUMENTS

JP H06209961 A 8/1994
JP H09502620 A 3/1997
(Continued)

OTHER PUBLICATIONS

International Search Report and Written Opinion issued in PCT/US2020/058581, date of mailing Feb. 25, 2021, 9 pages.
(Continued)

*Primary Examiner* — Steven A. Reynolds
(74) *Attorney, Agent, or Firm* — Fenwick & West LLP; Matthew Pavao; Brian Hopkins

(57) ABSTRACT

Embodiments of the present disclosure are directed to a biomedical packaging system which may include an assembly/primary packaging having one chamber configured to hold liquid nutrient media, as well as a bio-artificial organ (BAO), and another chamber arranged adjacent to the first compartment configured to be substantially liquid-free. The system can further include a baffle including a port, configured to separate the first chamber from the second chamber, as well as a storage container/secondary packaging.

15 Claims, 4 Drawing Sheets

(51) Int. Cl.
    *A61F 9/00*           (2006.01)
    *B65D 81/22*        (2006.01)

(52) U.S. Cl.
    CPC ................ *A61F 2220/0008* (2013.01); *A61F 2250/0068* (2013.01)

(58) Field of Classification Search
    USPC ................................................ 206/438, 363
    See application file for complete search history.

(56) References Cited

U.S. PATENT DOCUMENTS

| | | | |
|---|---|---|---|
| 5,385,229 A | | 1/1995 | Bittmann et al. |
| 5,653,688 A | | 8/1997 | Mills et al. |
| 5,720,391 A | * | 2/1998 | Dohm ................... A61F 2/0095 206/583 |
| 5,868,253 A | * | 2/1999 | Krueger ................ A61F 2/0095 206/583 |
| 5,904,144 A | | 5/1999 | Hammang et al. |
| 5,945,075 A | * | 8/1999 | Chiron ................... A61B 50/30 206/592 |
| 6,199,696 B1 | * | 3/2001 | Lytle ..................... A61F 2/0095 53/409 |
| 6,361,771 B1 | | 3/2002 | Tao et al. |
| 7,115,257 B1 | | 10/2006 | Tao et al. |
| 7,648,030 B2 | * | 1/2010 | Landis ................... A61F 2/0095 206/592 |
| 7,669,716 B2 | * | 3/2010 | Lightner ........... B65D 77/0453 206/583 |
| 9,265,814 B2 | | 2/2016 | Kauper et al. |
| 10,195,140 B2 | | 2/2019 | Mcgovern et al. |
| 2003/0168370 A1 | * | 9/2003 | Merboth .............. A01N 1/0263 206/438 |
| 2004/0221719 A1 | | 11/2004 | Wright et al. |
| 2007/0125099 A1 | | 6/2007 | Butler |
| 2008/0128296 A1 | | 6/2008 | Stopek et al. |
| 2008/0286323 A1 | | 11/2008 | Tornoe et al. |
| 2011/0214398 A1 | * | 9/2011 | Liburd ................... B65D 77/26 53/467 |
| 2011/0236457 A1 | | 9/2011 | Kauper et al. |
| 2013/0118126 A1 | * | 5/2013 | Hulliger ................ A61F 2/0095 53/167 |
| 2014/0299498 A1 | * | 10/2014 | Neal ......................... A61J 1/00 53/473 |
| 2015/0073381 A1 | | 3/2015 | Kauper et al. |
| 2024/0180686 A1 | | 6/2024 | Kauper et al. |

FOREIGN PATENT DOCUMENTS

| | | |
|---|---|---|
| JP | H09-089881 A | 4/1997 |
| JP | 2000507854 A | 6/2000 |
| WO | WO-9118575 A1 | 12/1991 |
| WO | WO-9501203 A2 | 1/1995 |
| WO | WO-9639027 A1 | 12/1996 |
| WO | WO-9734586 A2 | 9/1997 |
| WO | WO-2021087476 A1 | 5/2021 |
| WO | WO-2021087481 A1 | 5/2021 |

OTHER PUBLICATIONS

International Preliminary Report on Patentability for Application No. PCT/US2020/058581, mailed May 12, 2022, 7 pages.
International Preliminary Report on Patentability for Application No. PCT/US2020/058589, mailed May 12, 2022, 10 pages.
International Search Report and Written Opinion issued in PCT/US2020/058589, date of mailing Apr. 14, 2021, 15 pages.

* cited by examiner

702

704

700

706

708

710

712

714

716

720

722

718

SYSTEM, APPARATUSES, DEVICES, AND METHODS FOR PACKAGING AN ANALYTE DIFFUSIVE IMPLANTABLE DEVICE

RELATED APPLICATIONS

This application is a U.S. National Phase application, filed under 35 U.S.C. § 371 (c), of International Application No. PCT/US2020/058581, filed Nov. 2, 2020, which. claims the benefit of and priority to U.S. provisional application No. 62/929,619, filed Nov. 1, 2019, and U.S. provisional application No. 62/930,504, filed Nov. 4, 2019, the contents of each of which are incorporated by reference in their entireties.

BACKGROUND OF THE DISCLOSURE

In packaging pharmaceutical agents, and medical devices, handling of the bioartificial organs (BAOs) is especially concerning given the necessity of keeping the BAO in a sterile condition, as well as maintaining the BAO in a condition for surgical use/implantation. For example, when packing and shipping bioartificial organs (BAOs), it is necessary to provide a package or container (which can be referred to as a packaging system) that provides a biologically appropriate volume of liquid nutrients so as to bathe and nourish the BAO. Additionally, in such a packaging system, it is also advantageous to: (1) maintain product sterility and impart mechanical protection (so as to minimize storage or transport damage), (2) maintain isolation of gases and/or liquids across boundaries of the packaging system, (3) maintaining the BAO in specific position (e.g., vertical, horizontal position), such that the BAO can be continuously submerged within the liquid volume, and (4) using the packaging system, or a component thereof, as a device/tool during a surgical procedure to facilitate transfer of the BAO from the packaging system to the surgical site by a clinician.

SUMMARY OF SOME EMBODIMENTS OF THE PRESENT DISCLOSURE

In some embodiments, a biomedical packaging system is provided, and includes, an assembly having one chamber (e.g., first or lower) configured to hold liquid nutrient media, as well as a bio-artificial organ (BAO), and another chamber (e.g., second or upper) arranged adjacent to the other chamber and configured to be substantially liquid-free. The system can further include a baffle including a port, configured to separate the chambers.

In such embodiments, at least one of the following additional features, functionality, structure, steps, and/or clarifications (and in some embodiments, a plurality of, and in some embodiments, all of) can be included, leading to yet further embodiments:

the second chamber (or first chamber) includes a flange;
at least one of the chambers, and in some embodiments, each chamber includes a wall;
the wall of the first chamber is integral with the wall of the second chamber;
the wall of at least one of the chambers includes a step configured to retain or otherwise hold a perimeter of the baffle;
the at least one of the perimeter of the baffle and the inner circumference of the wall of the first and/or the second chamber includes a material configured to seal the perimeter of the baffle with the wall of the first and/or the second chamber;

the second chamber is sealed with a non-permeable membrane on or over the flange;
the port is centrally arranged on the baffle;
the port is closed via at least one closure system;
the baffle is configured with a pitch;
where the pitch can be configured from an edge of the baffle to the center of the baffle;
the pitch can be between approximately 5 and 30 degrees;
the baffle can be configured to vent gas during the filling of the first chamber with liquid;
the baffle can be sealed to at least one of the first and second chambers;
sealing can comprise ultrasonic welding;
the closure system can be configured:
with threaded engagement; and
as a plug; or
as a plug and a corresponding receptacle, where the plug and the receptacle can be configured to couple together via threaded engagement, and optionally:
a luer taper can be included in the plug and the receptacle;
the plug and the receptacle can be configured or further configured to frictionally fit together;
the closure system can further comprise a seal which may be tapered, and may also include at least one o-ring arranged on a/the plug, and optionally, the receptacle includes at least one corresponding recess configured to receive the at least one o-ring;
a storage container configured to house the assembly;
at least a portion of one or more of the first chamber, the second chamber, the baffle, and the storage container can be manufactured of a material having at least one of the following characteristics: transparency, medical grade, durable, non-degradable and substantially free from excipient release over time during exposure to elevated temperatures, pH and/or humidity;
at least a portion of one or more of the first chamber, the second chamber, the baffle, and the storage container can be manufactured of at least one of the following: polycarbonate, polyesters, polyetheramide, polyethylene terephthalate, and polyethylene co-glycol terephthalate;
upon a/the closure system including at least one of the plug and the receptacle, each may include a mating portion for receiving at least one of a medical device or a BAO;
and
the port of the baffle includes a neck portion configured to receive at least one of the plug and the receptacle, where the at least one of the plug and the receptacle and the neck portion can include corresponding mating means configured to connect the at least one of the plug and the receptacle with the neck portion.

These and other embodiments, objects and advantages will become even more evident with reference to the concurrently filed figures, a brief description of which is set out below, and following detailed description of at least some of the embodiments.

DETAILS OF AT LEAST SOME OF THE EMBODIMENTS

Figure 1:
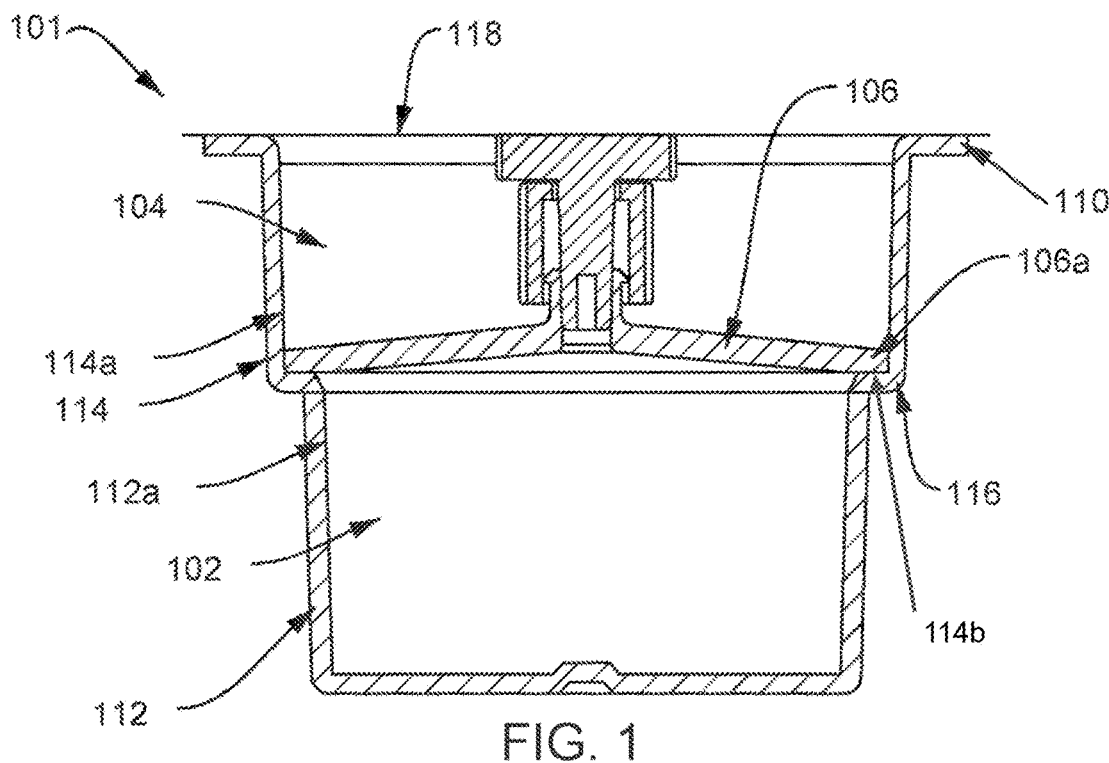
FIG. 1 illustrates a cross-section of a packaging assembly according to some embodiments of the disclosure.
Figure 2:
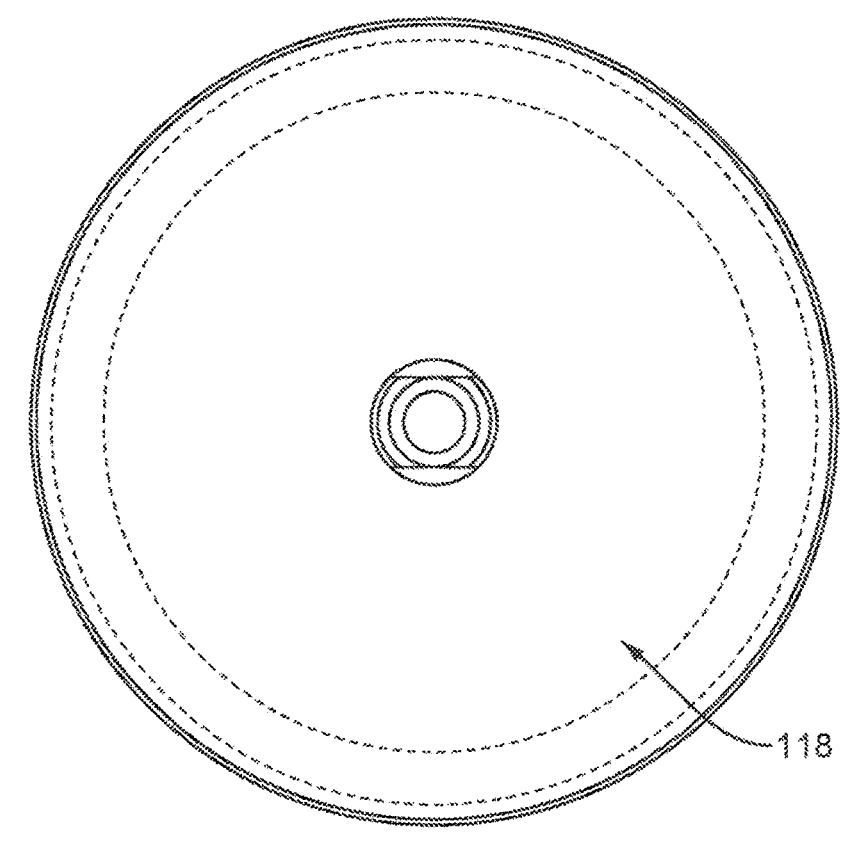
FIG. 2 illustrates a top view of a packaging assembly according to some embodiments of the disclosure.
Figure 3:
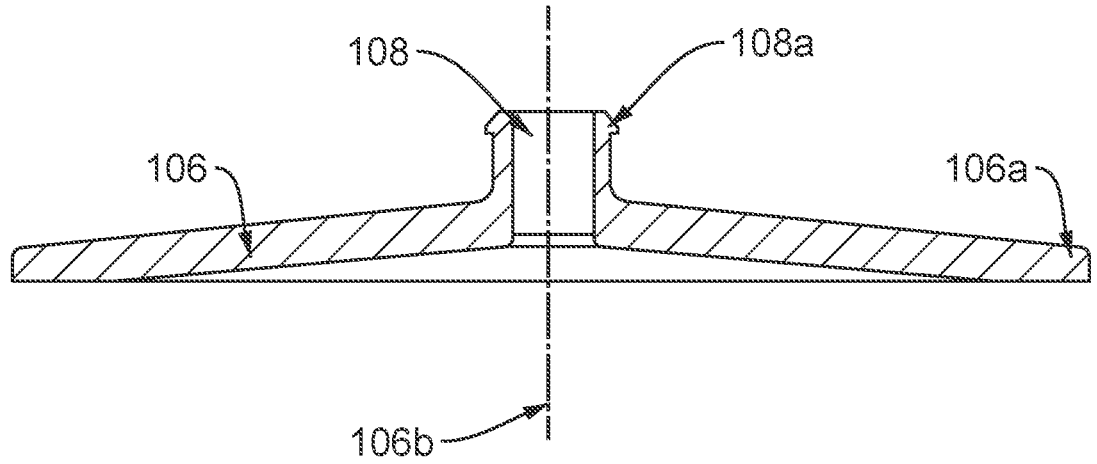
FIG. 3 illustrates a cross-sectional view of a baffle for at least separating chambers of a packaging assembly according to some embodiments of the disclosure.

FIGS. 1-7 illustrate various embodiments of the subject disclosure. A biomedical packaging system 100 (see FIG. 5) includes, as shown in FIG. 1, an assembly 101 having a first chamber 102 configured to hold liquid nutrient media, as well as a bio-artificial organ (BAO), and a second chamber 104 arranged adjacent to the first chamber 102 and configured to be substantially liquid-free. The system can further include a baffle 106 including a port 108, configured to separate the first chamber 102 from the second chamber 104.

In such embodiments, the second chamber can include a flange 110, and at least one of the chambers 102 and 104, and in some embodiments, each chamber, includes a wall 112, 114. The wall 112 of the first chamber 102 can be integral with the wall 114 of the second chamber. The wall 114 of the second chamber 104 can include a step 116 which can be configured to retain or otherwise hold a perimeter 106a of the baffle 106 (see FIGS. 2-3). The wall 114 of the second chamber 104 can include a recess or ledge 114b which can be configured to retain or otherwise hold a/the perimeter 106a of the baffle 106. The at least one of the perimeter 106a of the baffle 106 and an inner circumference 112a, 114a of the wall of the first and/or the second chamber 102, 104, includes a material configured to seal the perimeter 106a of the baffle 106 with the wall 112, 114 of the first and/or the second chamber 102, 104.

The second chamber 104 can be sealed with a non-permeable membrane 118 on or over the flange 110. In some embodiments, the port 108 can be centrally arranged on the baffle 106, and the port 108 can be closed via at least one closure system 120.

In some embodiments, the baffle is configured with a pitch, where the pitch can be configured from an edge 106a of the baffle 106 to the center 106b of the baffle, and the pitch can be between the pitch can be between approximately 5 and 30 degrees, and the baffle can be configured to, for example, vent gas during filling of the first chamber 102 with liquid. The baffle 106 can be sealed to at least one of the first and second chambers, where sealing can comprise ultrasonic welding.

Figure 4:
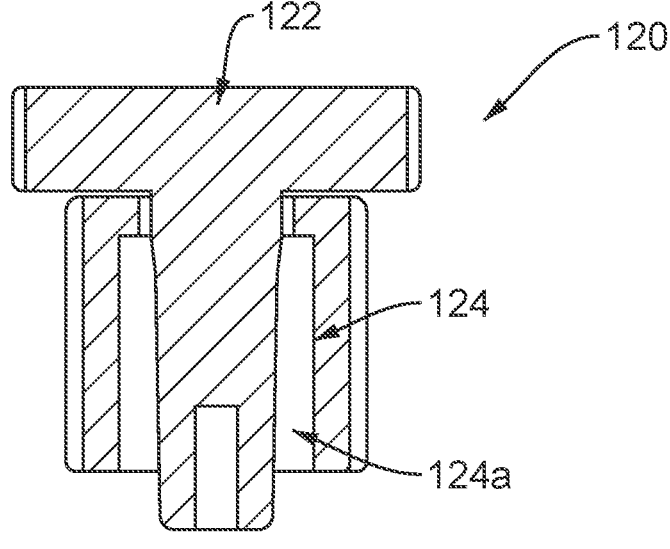
FIG. 4 illustrating a cross-sectional view of a plug and receptacle for a packaging assembly/system according to some embodiments.
Figure 5:
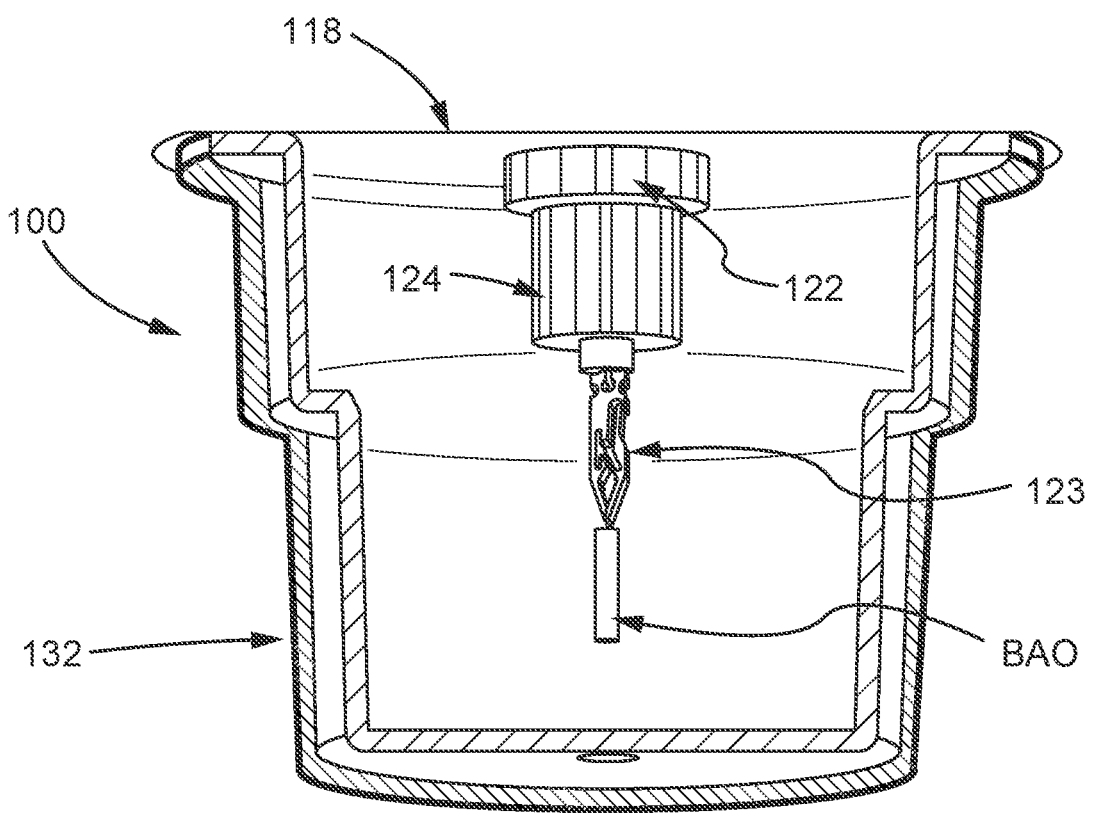
FIG. 5 illustrates a perspective view, which also shows internal structures, of the packaging system showing the assembly housed/nested within a storage container, according to some embodiments.
Figure 6:
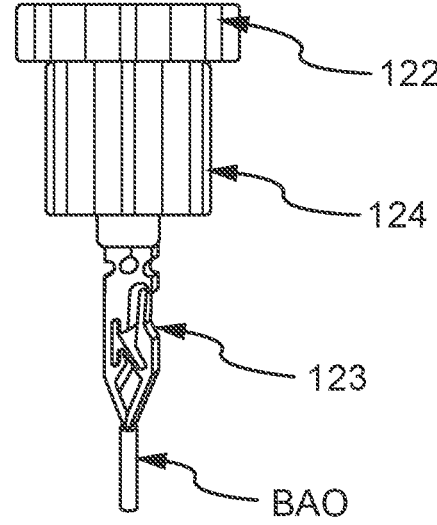
FIG. 6 illustrates a perspective/side view, which also shows internal structure, of a plug and receptacle configuration for holding a biological tissue within a chamber of the assembly, according to some embodiments.

As shown in FIGS. 4 and 6, in some embodiments, the closure system 120 can be configured for threaded engagement, and as a plug 122, or as a plug and a corresponding receptacle 124, where the plug 122 and the receptacle 124 can be configured to couple together via threaded engagement (for example). Optionally, a luer taper can be included in the plug and the receptacle, and/or the plug 122 and the receptacle 124 can be configured or further configured to frictionally fit together. The closure system 120 can further comprise a seal (not shown) which may be tapered, and may also include at least one o-ring (not shown) arranged on a/the plug 122, and optionally, the receptacle 124 includes at least one corresponding recess (not shown) configured to receive the at least one o-ring. In some embodiments, the system can also include a storage container 132 configured to house the assembly 101. As shown in FIG. 5, the storage container 132, according to some embodiments, can be designed or otherwise configured in a shape and size so as to nest the assembly within the container. For example, the nested configuration can hold the assembly in a substantially rigid configuration, and/or provide support for the assembly housed there within.

In some embodiments, at least a portion of one or more of the first chamber 102, the second chamber 104, the baffle 106, and the storage container 132 can be manufactured of a material having at least one of the following characteristics: transparency, medical grade, durable, non-degradable and substantially free from excipient release over time during exposure to elevated temperatures, pH and/or humidity.

In some embodiments, at least a portion of one or more of the first chamber 102, the second chamber 104, the baffle 106, and the storage container 132 can be manufactured of at least one of the following: polycarbonate, polyesters, polyetheramide, polyethylene terephthalate, and polyethylene co-glycol terephthalate.

Upon a/the closure system 120 including at least one of the plug 122 and the receptacle 124, each may include a mating portion configured to receive, for example, a clip 123 for holding or otherwise retaining at least one of a medical device or a BAO. In some embodiments, the port 108 of the baffle 106 includes a neck portion 108a configured to receive at least one of the plug 122 and the receptacle 124 (e.g., area 124a), where the at least one of the plug 124 and the receptacle 124 and the neck portion 108a can include corresponding mating means configured to connect the at least one of the plug 122 and the receptacle 124 with the neck portion 108a.

Figure 7:
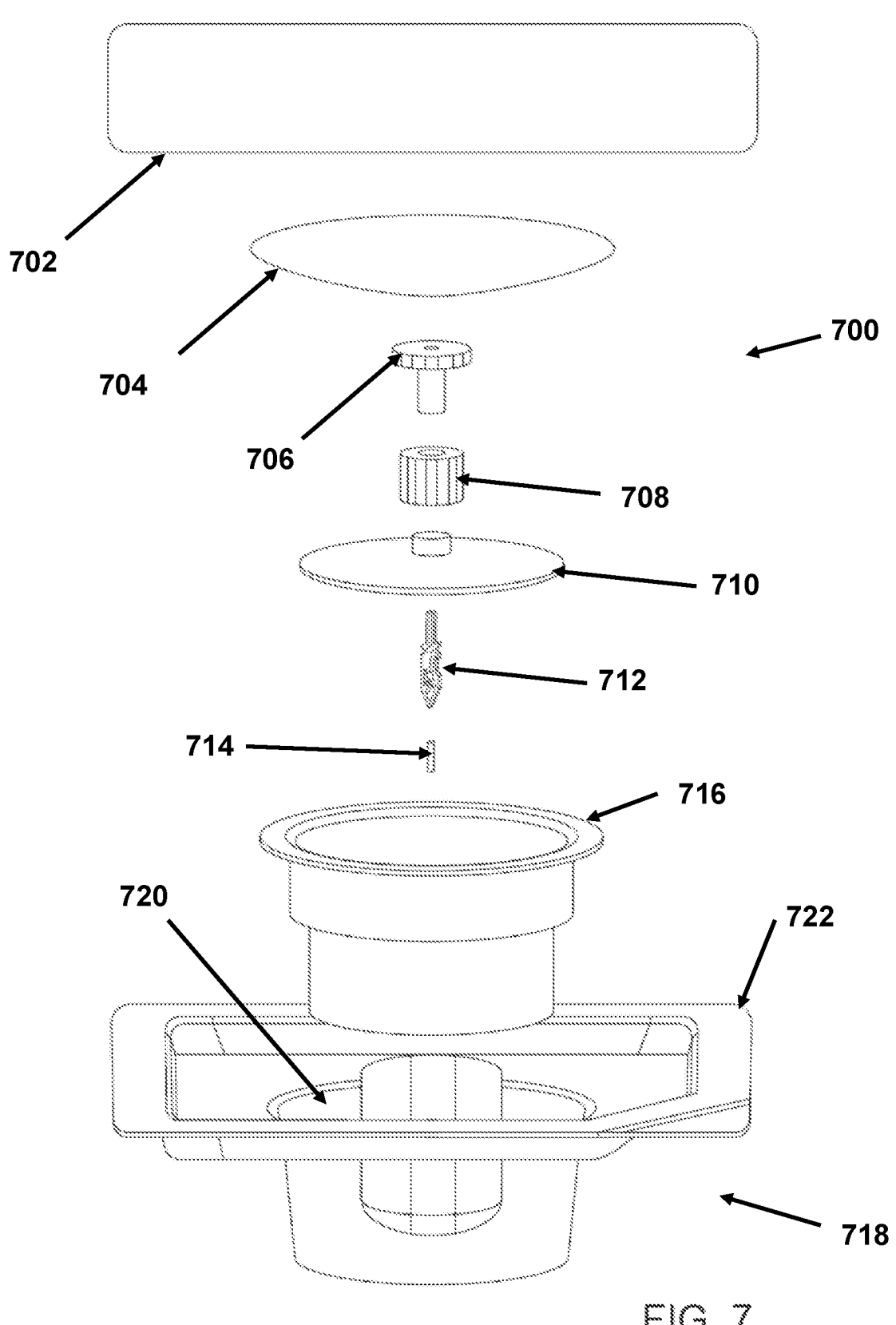
FIG. 7 illustrates a perspective, exploded view of a packaging assembly/system, according to some embodiments.

FIG. 7 represents yet another aspect of a packaging system according to some embodiments of the present disclosure. As shown, packaging system 700 includes primary packaging component 718 (which may also be referred to as an assembly; see also FIGS. 1-6 and above description), which houses BAO 714, clip 712, primary packaging baffle 710, a receptacle including plug (which may also be referred to as a baffle cap) 706 and locking ring 708 (which may itself be considered a "plug"), and a primary packaging lid 704. The packaging system, according to such embodiments, may further include a secondary package, comprising base 708, which includes a recess 720 for receiving the primary package base (as well as items packaged therein, and lid 704). The secondary package may include an upper portion 722, which includes a rectangular shape, which may aid in shipment of the packaging system. In some embodiments, the secondary package may also be referred to as a storage container (e.g., see ref. no. 132, with respect to FIG. 5, although the secondary package, in some embodiments, may house the assembly and container with respect to FIG. 5).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims, equivalents thereto, and any claims supported by the present disclosure, inventive embodiments may be practiced otherwise than as specifically described and claimed. Inventive embodiments of the present disclosure are directed to each individual feature, system, article, material, kit, method, and step, described herein. In addition, any combination of two or more such features, systems, articles, materials, kits, methods, and steps, if such features, systems, articles, materials, kits, methods, and steps, are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A biomedical packaging system comprising an assembly comprising:

a single, integral, circumferential side wall;

a first chamber configured to hold liquid nutrient media and a bio-artificial organ (BAO) and including a first side wall that comprises a first portion of the single, integral circumferential side wall;

a second chamber arranged adjacent to the first compartment and configured to be substantially liquid-free and including a second side wall that comprises a second portion of the single, integral circumferential side wall; and a baffle including a port, the baffle being configured to separate and seal off the first chamber from second chamber when the port is closed, such that material from the first chamber cannot flow or otherwise transfer into the second chamber.

2. The system of claim 1,
wherein the second chamber includes a flange;

the single, integral circumferential wall includes a step between the first portion and the second portion thereof which is configured to retain or otherwise hold a perimeter of the baffle.

3. The system of claim 2, wherein a pitch of the baffle is between approximately 5 and 30 degrees.

4. The system of claim 1, wherein the baffle is configured to vent gas during the filling of the first chamber with liquid.

5. The system of claim 1, wherein the baffle is sealed to at least one of the first and second chambers.

6. The system of claim 2, wherein the system further comprises a closure system which comprises a plug.

7. The system of claim 2, further comprising a closure system which comprises a plug and a corresponding receptacle.

8. The system of claim 7, wherein the plug and the receptacle are configured or further configured to frictionally fit together.

9. The system of claim 2, further comprising a closure system further comprises a seal.

10. The system of claim 7, wherein:

at least one of the plug and the receptacle includes a mating portion for receiving at least one of a medical device or a BAO; and/or the port of the baffle includes a neck portion configured to receive at least one of the plug and the receptacle.

11. The system of claim 10, wherein the at least one of the plug and the receptacle and the neck portion include corresponding mating means configured to connect the at least one of the plug and the receptacle with the neck portion.

12. The system of claim 1, further comprising a storage container.

13. The system of claim 12, wherein at least a portion of one or more of the first chamber, the second chamber, the baffle, and the storage container are manufactured of a material having at least one of the following characteristics: transparency, medical grade, durable, non-degradable and substantially free from excipient release over time during exposure to elevated temperatures, pH and/or humidity.

14. The system of claim 1, wherein:

the second chamber includes a flange, and at least one of the perimeter of the baffle and an inner circumference of a step portion of the single, integral, circumferential wall includes a material configured to seal the perimeter of the baffle with the step portion.

15. The system of claim 1, wherein:

the second chamber is sealed with a non-permeable membrane on or over a flange; the port is centrally arranged on the baffle;

the port is closed via at least one closure system; and/or the baffle is configured with a pitch, and the pitch is configured from an edge of the baffle to the center of the baffle.

* * * * *